(12) United States Patent
Neuberger et al.

(10) Patent No.: US 6,270,342 B1
(45) Date of Patent: Aug. 7, 2001

(54) DENTAL LASER TREATMENT HAND-PIECE AND SYSTEM

(75) Inventors: Wolfgang Neuberger, F. T. Labuan (MY); Michael Quade, Bonn (DE)

(73) Assignee: CeramOptec Industries, Inc., Easr Longmeadow, MA (US)

( * ) Notice: Subject to any disclaimer, the term of this patent is extended or adjusted under 35 U.S.C. 154(b) by 0 days.

(21) Appl. No.: 09/362,378

(22) Filed: Jul. 28, 1999

(51) Int. Cl.[7] .................................................. A61C 1/05
(52) U.S. Cl. ................... 433/29; 433/84; 433/86; 433/132; 310/4 MM
(58) Field of Search .................. 433/29, 77, 82, 433/84, 114, 131, 132, 86; 310/40 MM, 113

(56) References Cited

U.S. PATENT DOCUMENTS

| | | | |
|---|---|---|---|
| 3,731,384 | * 5/1973 | Brooks et al. | 433/132 |
| 3,932,055 | 1/1976 | Flatland . | |
| 4,642,738 | * 2/1987 | Meller | 433/29 |
| 5,192,279 | 3/1993 | Samuels et al. . | |
| 5,286,194 | * 2/1994 | Moriuchi et al. | 433/132 |
| 5,310,344 | 5/1994 | Vassiliadis et al. . | |
| 5,622,501 | 4/1997 | Levy . | |
| 5,752,829 | 5/1998 | Goldsmith et al. . | |
| 5,759,031 | 6/1998 | Goldsmith et al. . | |
| 5,785,521 | 7/1998 | Rizoiu et al. . | |
| 5,800,172 | * 9/1998 | Goldenberg | 433/29 |
| 5,846,080 | 12/1998 | Schneider . | |
| 5,851,112 | 12/1998 | Diakuzono et al. . | |
| 5,897,314 | 4/1999 | Hack et al. . | |
| 5,982,059 | * 11/1999 | Anderson | 310/40 MM |

* cited by examiner

Primary Examiner—Todd E. Manahan
(74) Attorney, Agent, or Firm—Bolesh J. Skutnik; BJ Associates

(57) ABSTRACT

A handpiece is presented which utilizes fluid channels instead of electric wiring to provide power to a treatment device. These fluid channels operate a micro-turbine generator that provides electrical energy to treatment devices. Each micro-turbine generator generates electrical energy for powering at least one electricity consuming functional device; wherein said electricity consuming functional device is selected from the group; a compact laser, an electromechanical dental drill, an ultrasound generator, a microwave generator and, an activator for treatment chemicals. In particular this device provides energy to a dental hand-piece without the need for electrical wiring or optics between the hand-piece and the control apparatus. One or more fluid channels permit fluids to flow between the control apparatus and the hand-piece. This flow of fluid operates the micro-turbine, which in turn produces energy to operate a medical/dental device. The fluid channels can also be used to deliver substances in conjunction with the medical device use. The hand-piece of this apparatus can be manufactured for a specific medical/dental procedure, or the apparatus can be made compatible/interchangeable with existing hand-pieces and control apparatus. This micro-turbine energy system provides the power necessary to operate many state of the art devices. For example, the energy produced can be used to operate a laser used for various dental applications such as drilling, pre-heating of the drill area, or activation of PDT substances.

20 Claims, 6 Drawing Sheets

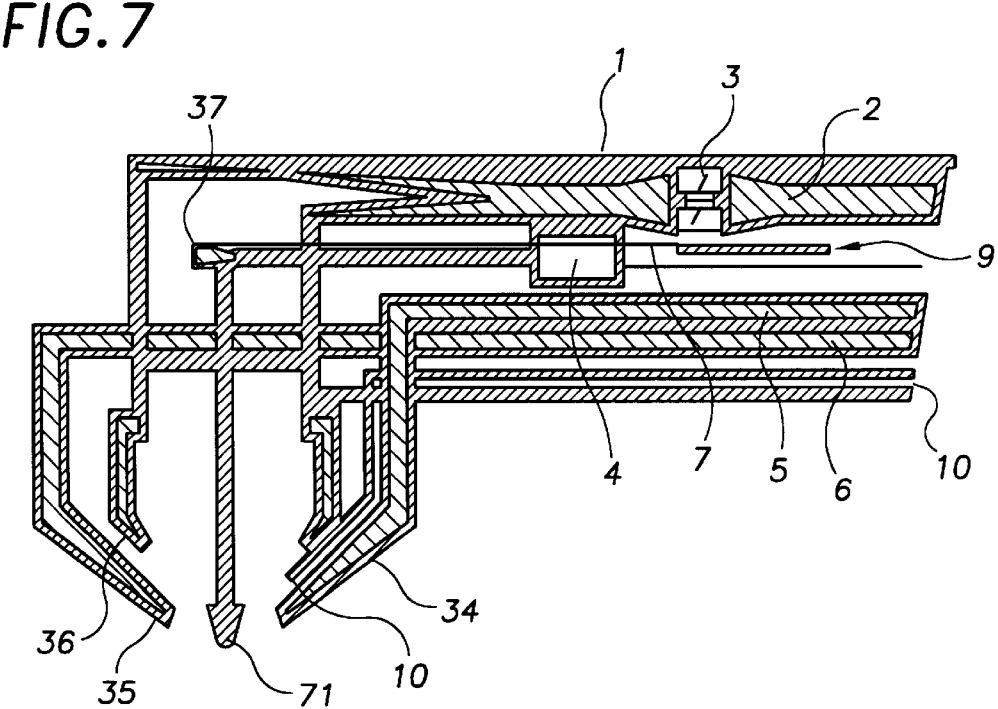
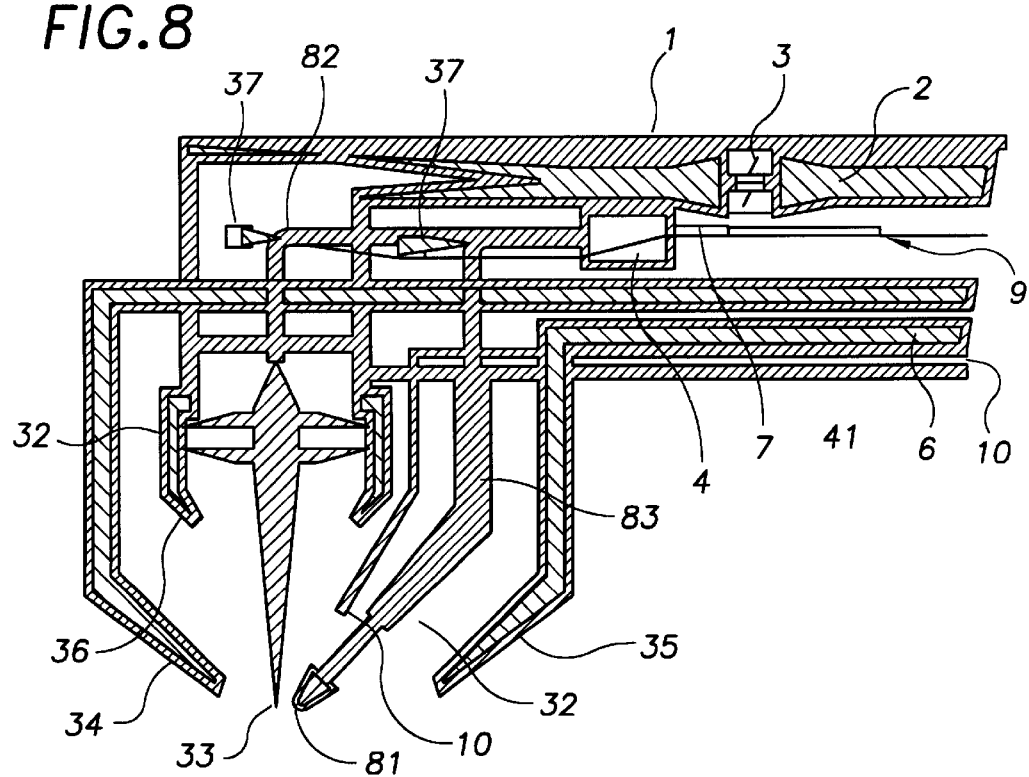

DENTAL LASER TREATMENT HAND-PIECE AND SYSTEM

BACKGROUND OF THE INVENTION

1. Field of the Invention

The present invention relates to small sealed handheld laser systems, which fulfill all clinical use requirements and which can be operated simply. In particular, this invention refers to laser hand-pieces for use in the dental field.

2. Invention Disclosure Statement

The general problem with medical or dental devices that employ electrical and/or mechanical tools is that it is difficult to separate the circuits and/or the machinery from parts of the body that don't require treatment. Any proximity between the patient and the working components that make up the treatment device, increases the risk of harm to the patient. The shielding materials used in the prior art however, increase the device size and restrict the treatment area. This restriction in treatment area size often means that a treatment can not be performed as effectively. This lack of efficiency can also mean that the medical procedure is not cost effective.

A typical hand-piece in the prior art consists of a drill and an electric power source in proximity to the patient. For example, U.S. Pat. No. 5,785,521 describes a combination drill and fluid conditioning system that delivers various fluids to the dental area. This system has the advantage of delivering fluids during drilling, but the device still has an electrically powered drill incorporated into the hand-piece.

Since electrical wiring imposes a multitude of safety restrictions, medical instruments need some alternative energy source. The prior art has made several attempts to solve this problem. In laser instruments, one solution has been to employ optical fibers to guide radiation from a peripheral laser source to the hand-piece and treatment site. This is illustrated in U.S. Pat. No. 5,310,344, which describes a state of the art dental laser system where the optical fiber is a single crystal sapphire strand. This sapphire strand is used to connect the laser housing to a dental hand-piece some distance away. The drawback to this concept is that optical fibers, especially crystal strands, can often break.

Another solution in laser dental applications has been to directly image laser radiation to the treatment site as described in U.S. Pat. No. 5,846,080. This system images laser radiation from a laser source in the system, to the distal end treatment site. This type of laser system however, is very cumbersome and is difficult to utilize in dentistry applications.

It is important to find a practical way to deliver laser radiation to the mouth region because lasers have multiple applications in dentistry. U.S. Pat. No. 5,192,279 describes the use of laser radiation to safely remove a carious lesion, desensitize the treatment area, or seal a dental tissue surface. U.S. Pat. No. 5,622,501 describes a system where the laser source is used in conjunction with a photochemical to destroy bacteria on tooth surfaces or in the oral cavity.

In the prior art, another solution to avoid the use of electricity in proximity to the patient has been to use liquid or gaseous streams in the place of an electric device. These fluid streams are delivered through a channel system to the hand-pieces. The use of pneumatic tools is applicable in dental drilling, to aspirate an area or to supply photodynamic substances, abrasive fluids, or anaesthetic drugs. This type of system can be used in abrasion or disinfecting procedures.

U.S. Pat. No. 5,759,031 and U.S. Pat. No. 5,752,829 describe an abrasive air system for use in the dental field. Its primary feature is an air abrasive drill system that is more accurate than previous air abrasive systems. This system incorporates a vacuum system to remove the abrasive materials as well as means for illuminating the target site. The problem with this invention is that it is a separate piece of equipment that is not necessarily compatible with any existing equipment.

One final solution, to avoid having electrical components in proximity with the patient, is the concept of a turbine dental drill. U.S. Pat. No. 3,932,055 describes a vacuum turbine dental drill. This invention has only limited applications since any other device that requires electrical energy cannot be used. Likewise, this invention can only be combined with a radiation source if optical fibers are used to reach the treatment area.

Various dental applications are generally accomplished by using a specialized hand-piece. The hand-pieces are manufactured to suit a particular application or treatment type. The hand-pieces must also be connected to a specific peripheral supply system. U.S. Pat. No. 5,851,112 describes an optical fiber hand-piece for use in various oral treatments. This hand-piece only incorporates a laser and any other devices needed for a procedure must be separately contained. U.S. Pat. No. 5,897,314 describes a hand-piece that is designed specifically for a root canal treatment. This hand-piece has limited used because it is a separate tool that can only be used for a single type of procedure.

The prior art has several problems that limit the use of lasers in dental applications. First each hand-piece system must be manufactured for a specific application. If a fiber is used to connect the hand-piece to a peripheral laser system, the fiber can only be used over limited distances. Although fibers are flexible, there is the danger of potential fiber breakage that would cause the device to malfunction. The fibers therefore must be protected with a surrounding material or sleeve to reduce the risk of breakage. Another difficulty is that the laser source must be part of a separate peripheral device with it's own cooling and power supply. Any other instruments needed for a procedure must be contained in a separate apparatus that has its own power supply. This limitation increases the space and cost requirements for implementing laser procedures. It is the goal of the present invention to provide a solution to these problems in the prior art.

BRIEF SUMMARY OF THE INVENTION

It is the principal object of the present invention to provide a hand-piece that does not put electrical circuitry in proximity with a patient.

It is an object of the current invention to provide a compact design for dental hand-pieces.

It is also an object of the present invention to provide a dental band-piece system that is compatible with existing devices.

The present invention utilizes fluid channels instead of electric wiring to provide power to the treatment device. These fluid channels operate a turbine generator that provides electrical energy to treatment devices. The present invention is compatible with existing pneumatic systems in any dental office and can also be used for a variety of medical applications. The turbine system and hand-piece are compact due to progress in miniaturized mechanics. This device is safer than the prior art because there is less risk of electrical shock, since all electrical circuitry is sealed within the hand-piece. Furthermore, the hand-piece is connected to a fluid supply so that there is no direct connection between the hand-piece and a external power supply.

Briefly stated, the present invention provides a novel device that utilizes a micro-turbine to provide energy to a medical or dental hand-piece. In particular this device provides energy to a dental hand-piece without the need for electrical wiring or optics between the hand-piece and the control apparatus. One or more fluid channels permit fluids to flow between the control apparatus and the hand-piece. This flow of fluid operates the micro-turbine, which in turn produces energy to operate a medical/dental device. The fluid channels can also be used to deliver substances in conjunction with the medical device use. The hand-piece of this apparatus can be manufactured for a specific medical/dental procedure, or the apparatus can be made compatible/interchangeable with existing hand-pieces and control apparatus. This micro-turbine energy system provides the power necessary to operate many state of the art devices. For example, the energy produced can be used to operate a laser used for various dental applications such as drilling, pre-heating of the drill area, or activation of PDT substances.

The above, and other objects, features and advantages of the present invention will become apparent from the following description read in conjunction with the accompanying drawings, in which like reference numbers in different drawings designate the same elements.

BRIEF DESCRIPTION OF FIGURES

FIG. 7 depicts a cross section of a specialized hand-piece for the cauterization of a surgical treatment area.

FIG. 8 depicts a cross section of a complex surgery tool with two turbine-driven laser systems to perform two different functions simultaneously.

DETAILED DESCRIPTION OF PREFERRED EMBODIMENTS

A purpose of this invention is to provide a device that reduces the need for electrical circuitry in proximity with the patient. Instead of electric current, a fluid flow delivers energy to the treatment zone. These fluids operate a turbine generator that provides the electrical energy to drive treatment devices that need electrical energy. This turbine generator is embedded in a particular hand-piece to serve the needs of a specific application. The present invention solves many of the mentioned problems with the prior art. First, the present invention is compatible with existing pneumatic systems in any dental system. It is also compact due to the progress in miniaturized mechanics. It is safer than the prior art because all working components are kept within a sealed hand-piece, thus reducing risk to the patient. Finally, the present invention serves as a basis for a plurality of medical applications.

Figure 1:
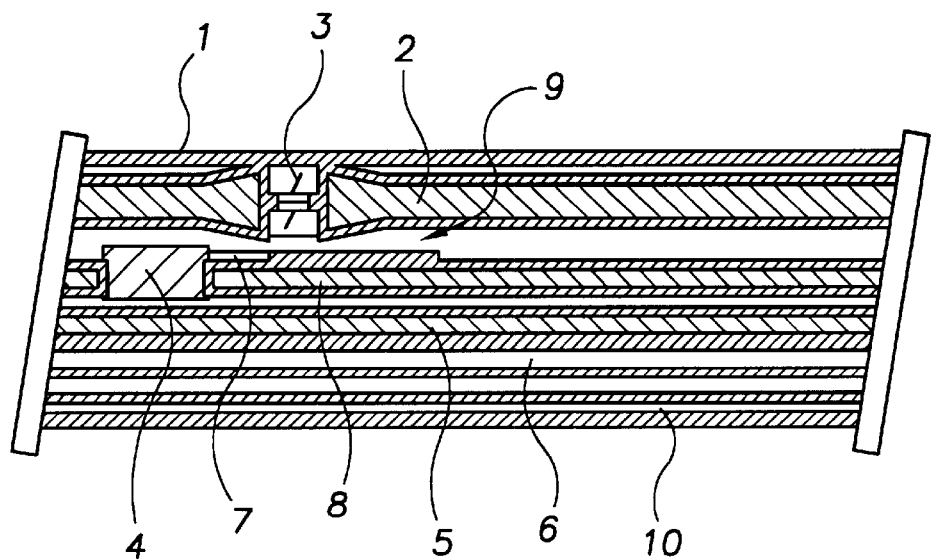
FIG. 1 shows a cross section of a basic hand-piece of the present invention without the application section of the hand-pieces.

The most basic embodiment of the present invention comprises a micro-turbine engine, a device powered by the energy produced, and a fluid to drive the micro-turbine. FIG. 1 shows a basic hand-piece of the present invention without the application section of the hand-piece. Sealed in outer shaft 1 there is at least one power fluid supply channel 2 with at least one micro turbine generator 3 enclosed. This sealed housing prevents any contact between the generated electrical energy and the treatment elements being used on the patient. Functional device 4 is enclosed in the hand-piece and is electrically connected to micro turbine generator 3 by isolated electrical circuitry 7. As a result of this isolation, the patient and medical staff are protected from any electrical discharge. The fluid passing through power fluid supply channel 2 drives micro-turbine generator 3. This fluid can be either a gas or a liquid. By changing the fluid pressure and flow rate, the power generation of the micro-engine will vary by predictable increments and can be easily controlled. A large amount of heat (>30 W) can be generated by the micro-turbine generator. The fluid used to drive the micro-turbine generator dissipates any heat produced by micro-turbine's operation.

To add flexibility to the device, the micro-turbine engine power can optionally be buffered by battery 9. Battery 9 allows a more consistent power output. Battery 9 is charged by micro-turbine engine 3. Functional device 4's power needs can be either supplemented or supplied by battery 9 if the power level from micro-turbine generator 3 drops below the required output. For example, if power fluid supply channel 2 is used to deliver fluids to the treatment site, battery 9 allows the flow rate to be varied for a more precise application of therapeutic fluids. The amount of fluid delivered to the treatment site can be more precisely controlled or even stopped for periods of time without affecting power to functional device 4.

Preferably power fluid supply channel 2 either recycles the fluid back to the control unit or connects directly to aspirating vacuum-channel 6 and another channel is used to deliver the therapeutic fluids. At least one secondary supply channel 5 is enclosed in the sealed hand-piece. This secondary channel system serves as a direct supply for additional therapeutic substances. The substances supplied by secondary channel 5 move directly in the channel from the control unit to either the treatment area or a secondary device. For example, these substances can be used for a fluid power supply to a conventional turbine drill. Secondary channel 5 could also be used as a direct supply for treatments such as abrasive procedures, PDT or anaesthetic methods.

The fluid channels can also be used in abrasive processes, in which solid particles are guided with the fluid and applied within the fluid beam to the treatment zone. In general, the particles are solid and can either be transparent or opaque to the laser radiation. Depending on the choice of transparent or opaque particles, the scattering effect of the laser radiation can be varied. Transparent particles generally preserve the laser beam direction and the diffusion takes place mainly as a homogenization in the beam direction. Opaque particles on the other hand diffuse the laser beam over a much broader area. It is therefore possible to vary the treatment zone from a restricted area to a broader area without exchanging the hand-piece. Examples of solid particles that are transparent, are glass, quartz or ice. Examples of solid particles that are opaque are $SiO_2$, sand or any ceramic substance generally used in conventional state of the art abrasive processes.

Functional device 4 serves as the power-consuming device in the hand piece. Functional device 4 is chosen to act on the treatment zone in either a direct or indirect way. Functional device 4 may consist of a laser system and be used for laser irradiation of a site. In an alternative, functional device 4 may be used to activate compounds employed in the treatment. One or more additional fluid channels 8 supply substances to the treatment area and are integrated into functional device 4. These substances can be activated within functional device 4 and then be delivered to the treatment zone through additional fluid channel 8.

At least one aspirating vacuum-channel 6 is included to remove particles and fluid from the treatment zone. Various substances generated or supplied during the treatment process can then be removed from the treatment zone. Aspirating vacuum-channel 6 can also be used to clean the treatment zone before the procedure begins.

A minimum of one optical fiber or fiber-bundle 10 is enclosed in the invention. Optical fiber 10 can be used for multiple applications. Optical fiber 10 can be used actively in either the unit function or on the treatment zone itself. It can also be used to observe treatment progress, as a diagnostic instrument or for endoscopic uses. Other elements of the present invention can contribute and be combined with the use of optical fiber 10. For example, if optical fiber 10 is used for diagnostic purposes, secondary supply channel 5 can supply substances that enhance the visibility of the treatment zone.

For any of the possible embodiments of power-consuming functional device 4, a hand-piece is designed to match the treatment and application requirements. Functional device 4 can be a high-powered diode laser, diode-pumped solid state laser, light-emitting diode, microwave components or ultrasound components. All of these particular options, however, may produce heat. The fluid supplied through additional fluid channel 8 cools functional device 4 to ensure that treatment conditions such as wavelength or generated power, do not vary with time.

The hand-piece includes power-measuring device 37 to regulate the light generated by functional device 4. Examples of suitable laser power measuring devices are photodiodes, transistors, piezoelectric elements as well as other state of the art detectors. These detectors should be chosen to correspond with the specific function of the various hand-pieces. The feedback from these detectors can either control the hand-piece function, or can interact with an external control unit. If for some reason the power generated by the device goes beyond the safe limit, an internal control mechanism is initiated to reduce or shut off power.

In one possible embodiment of the current invention, specially designed wave-guides are included for microwave components, such as gunn-diodes. In yet another possible embodiment piezoelectric elements can serve as ultrasound generators. These piezoelements can either drive oscillating elements for plaque removal and tooth polishing, or the signal can be coupled into a suitable ultrasound guide. Any combination of the aforementioned embodiments is possible in practical use. For example, microwaves can be employed for preheating dental tissue or teeth in order to enhance drilling, cutting or abrasion effects. Ultrasound can also be used in a similar way. Photodynamic chemicals are primarily used for disinfecting or to enhance a visual image, but they can be also used as an anesthetic as well.

Figure 2:
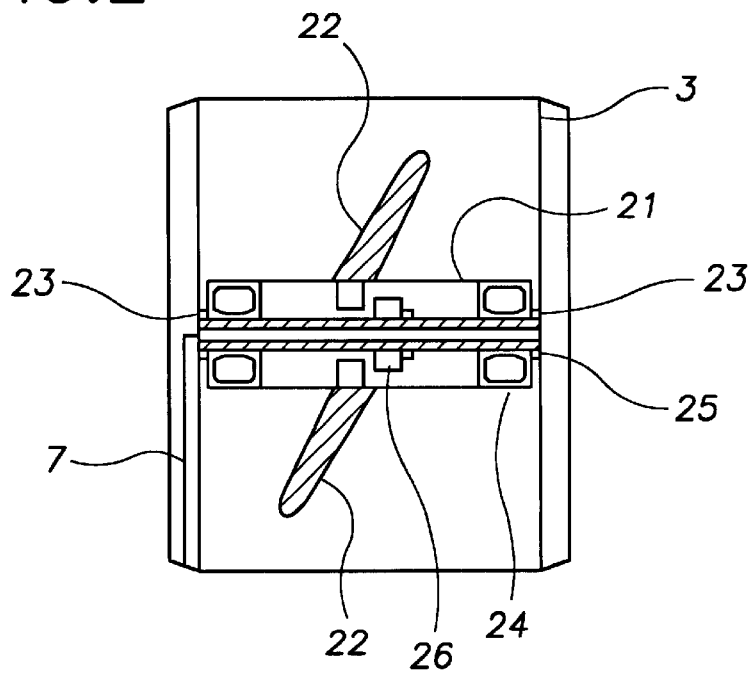
FIG. 2 shows cross section of a more detailed illustration of a micro-turbine generator of the present invention.

FIG. 2 shows a more detailed illustration of a micro-turbine generator. FIG. 2 illustrates the important innovative elements of this invention. Micro-turbine engine 3 includes a sealed housing at a given point along the fluid stream. The sealed housing only allows the fluid stream to pass along turbine wheel 21. The fluid turning turbine blades 22 drives turbine wheel 21. Roller bearings 23 and 24 are included to minimize frictional losses occurring between turbine wheel 21 and rotation axis 25. Roller bearings 23 and 24 also seal the turbine wheel from the fluid. Enclosed inside the turbine wheel is generator 26 of electrical energy. Generator 26 is completely isolated from the exterior, and particularly from any driving fluid. This generator can also be kept outside the micro-turbine itself if a mechanical connection between the micro-turbine and a micro-generator is utilized. Isolated electrical circuitry 7 connects the generating elements in turbine wheel 21 to functional device 4, which consumes the generated energy produced by micro-turbine generator 3. The housing of micro turbine generator 3 and turbine elements 21, 22, 23, 26 and 24 are made of a material that is dielectric and that can withstand the high pressure applied by the passing fluid. Turbine blades 22 and turbine wheel 21 are designed to minimize friction losses from the fluid, therefore optimizing the conversion efficiency of mechanical to electrical energy. The material is also chosen to resist corrosion by therapeutic substances, chemicals applied during the treatment and any abrasive micro-particles small enough to pass through the micro-turbine engine.

The present invention provides a hand-piece that is useful and can be applied in a clinical environment with the existing equipment. The present invention also provides fully functional equipment that can be extended by existing state of the art dental elements using a simple connector. The hand-pieces described in the current invention, however have the common advantage of being equally compatible with existing systems and the present invention apparatus as illustrated in FIG. 10.

Figure 10:
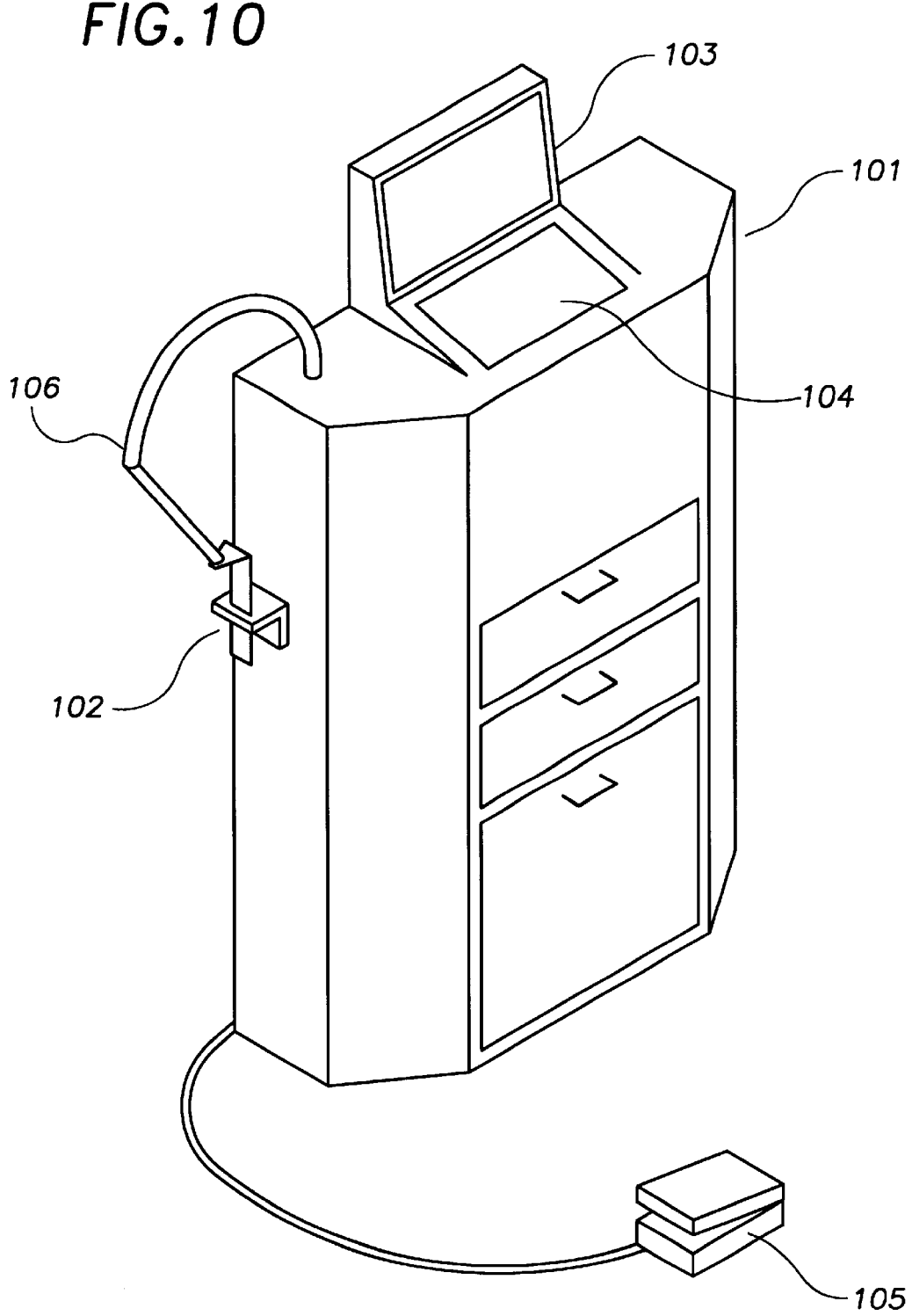
FIG. 10 shows an embodiment of the present invention control apparatus.

Another aspect of the present invention is the control unit illustrated in FIG. 10. All necessary treatment fluids are enclosed in suitable containers within rack/cabinet 101. Included in the control unit is at lest one turbine pump to generate pressure on the fluid sufficient to drive the micro-turbine generator in a chosen hand-piece. The control unit is designed so that it is possible add therapeutic and treatment substances to the fluid stream. Another turbine pump is enclosed in the apparatus to generate the secondary fluid stream for secondary supply channel 5. This secondary channel supplies fluid directly to the treatment area or a secondary device. The supply is designed so that additives can be placed into the fluid stream. The apparatus also includes a vacuum pump connected to aspirating vacuum channel 6.

Integrated into this rack is the central control unit. This unit allows the total control over the treatment method depending on which hand piece 102 is chosen. The central control consists of a microprocessor system with display monitor 103 and a keyboard 104. A protective covering encloses monitor 103 and keyboard 104 in order to maintain a sterile clinical atmosphere. This covering can be either removable for cleaning or disposable.

The clinical apparatus includes foot-piece 105, which allows certain parameters to be changed manually. For example, foot-piece 105 can be used to vary the fluid stream pressure or volume in the various channels. These variables when changed may in turn interact with aspirating vacuum channel 6 or device 4. The central unit also includes additional controls to regulate other dental or medical equipment. This central control unit can be compatible with standard equipment such as a turbine drill system. The control is designed to allow remote input and control from an outside device via suitable interfaces.

At least one hand piece is connected via flexible channel system 106 to the control apparatus as depicted in FIG. 10. Any number of hand pieces could be connected to the control apparatus. The interface between hand pieces and connecting channel system 106 is designed so that the hand-pieces are interchangeable. The hand-pieces are connected to the control unit via sterile connecting channel system 106. The channels should be flexible, so that the treatment process is not impaired. Furthermore channel system 106 is made of a durable and dielectric material. This ensures that none of the functional device elements come in contact with the patient.

The control system may also include a heat exchanger to provide sufficient cooling power for all the included systems. In another possible embodiment, the control unit may include a digital image processor. This allows inspection of the treatment zone via an optical fiber or suitably designed fiber system. This endoscopic function is integrated into a specific hand piece. At the proximal end of the endoscope, the treatment zone is imaged onto a CCD camera, which can be viewed on a standard monitor or computer system. This imaging enhances the control over the treatment, as well as the reliability and the reproducibility of the results. This endoscope can be used to illuminate and image the diseased or infected parts of the treatment area. This imaging allows a faster diagnosis and reduces treatment time. This also allows the same hand-piece to be used to monitor and perform the procedure.

A preferred embodiment of the present invention includes a closed and complete clinical apparatus that is the basic control and supply module for the hand-pieces. These hand-pieces allow various dental treatments to be performed. Since this invention can be used for multiple dental treatments, a variety of elements to the present invention are described. The present invention is further illustrated by the following examples, but is not limited thereby.

EXAMPLE 1

Figure 3:
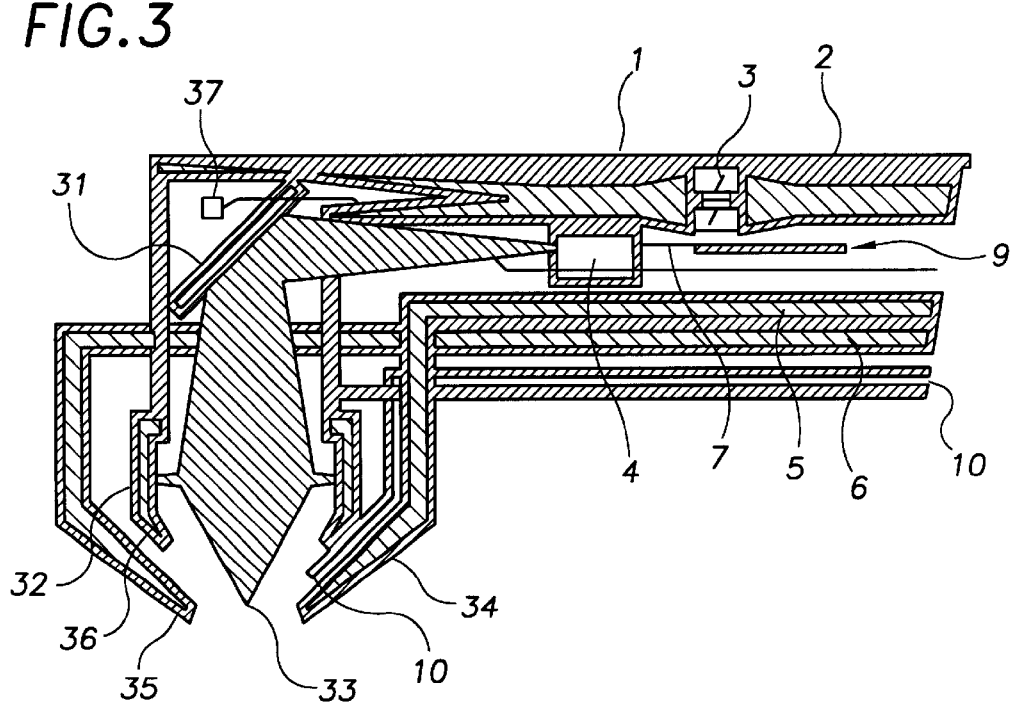
FIG. 3 illustrates a cross section of a laser hand-piece embodiment for dental applications.

A preferred embodiment of a hand-piece for dental applications is illustrated in FIG. 3. This particular embodiment can be employed for any general laser surgery or for dental tissue treatment. The hand-piece contains micro turbine engine 3, power fluid supply channel 2 to drive micro turbine generator 3, additional fluid supply channel 8 to functional device 4, secondary supply channel 5 and aspiration vacuum channel 6. Power fluid supply channel 2 terminates/empties near treatment zone 33 after passing micro turbine generator 3. The fluid itself can additionally serve to cool the treatment zone.

In this embodiment, functional device 4 is a semiconductor diode laser, which can produce radiation in a wavelength range of 400 to 3000 nm and an output power of up to 50 W in either cw or pulsed mode. The embodiment also includes power-measuring device 37, which can be enclosed in several ways. It is placed in such a way that it can detect the radiation that is back scattered from the surfaces of the optical system. Scattered laser radiation is absorbed in secondary supply channel 5. This absorption has a cooling effect and prevents the hand-piece from overheating. The diode laser radiation is suitably shaped and propagates towards treatment zone 33. In order to direct the radiation correctly, the device includes folding mirrors 31 and focussing optics 32. The entire hand-piece is sealed so that only focussing optics 32 serve as an interface to the exterior. Focussing optics 32 are designed to focus the radiation and create an area of sufficient intensity to achieve the desired therapeutic effect. The optics themselves are kept a sufficient distance away to prevent contamination.

The fluid from power fluid supply channel 2 can either flow directly out to the treatment zone or can be pressed through valves 36. Valves 36 are designed to create either another fluid ring or a straight form fluid beam. Secondary supply channel 5 is separate from power fluid supply channel 2. Secondary supply channel 5 can be used for general cooling, as a safety element for the hand-piece itself, as a separate cooling device, or as a treatment area fluid-supply 34 to provide additional substances which are needed at the treatment area. Secondary supply channel 5 can also be arranged either in a ring or straight form. The variation of supply channels can be used for various applications. For example, a tightly focused fluid beam can be used to make an incision and a laser beam can follow this beam to cauterize the tissue.

Optical fiber 10 is included in the hand-piece to allow viewing of the treatment site. Optical fiber 10 is connected to an imaging unit at the proximal end of the fiber. This imaging unit is a part of the central control unit included in the description of FIG. 10. Additional fibers can be added in order to achieve optimal operation of the device and provide a sufficiently clear image of the treatment zone.

Aspirating vacuum channel 6 has its intake area 35 in the vicinity of the treatment zone. The proximal end of aspirating vacuum channel 6 is connected to a vacuum pump. This pump generates a sufficiently low pressure to aspirate all treatment products, added fluids and particles included, saliva, or other body liquids which could be of negative effect to the treatment process. Although only one aspirating vacuum channel is depicted in FIG. 3, additional lines can be added in order to optimize the aspiration process. Furthermore, the distal end of aspiration vacuum channel 6 can be constructed as a small suction area or as a ring that surrounds the complete treatment area.

EXAMPLE 2

Figure 4:
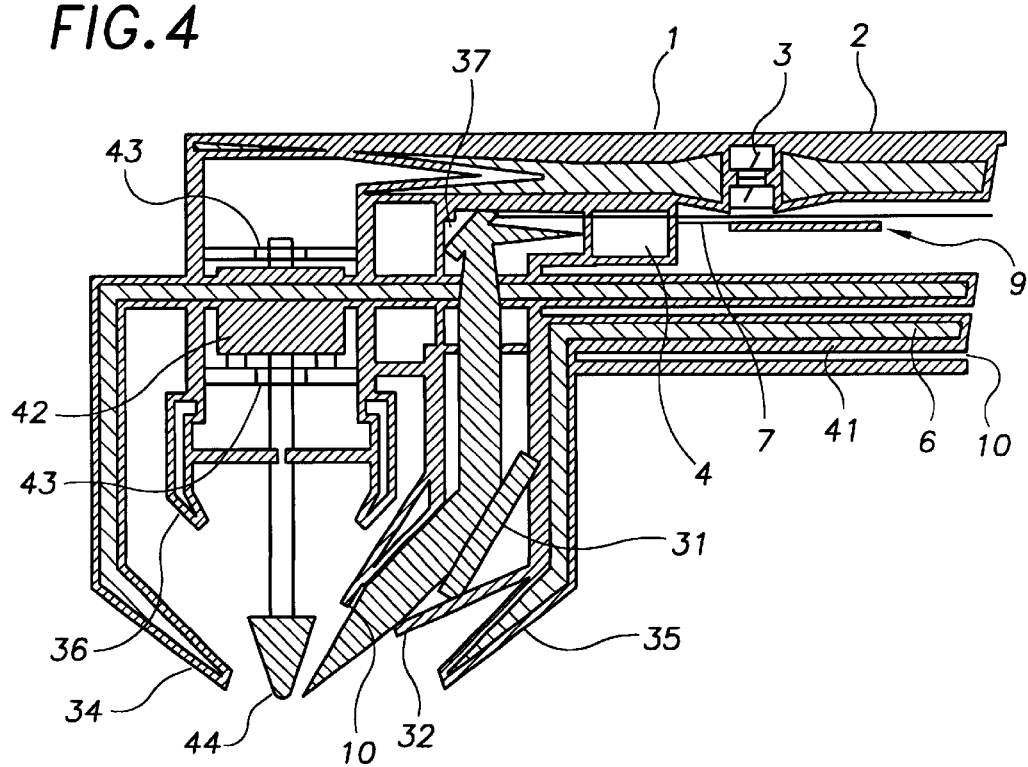
FIG. 4 illustrates a cross section of a hand-piece that combines a turbine driven laser and a conventional turbine dental drill.

FIG. 4 illustrates a hand-piece that combines a turbine generator driven laser and a conventional turbine drill. Turbine drill 42 is driven by secondary supply channel 5. Drill axis 43 is perpendicular to the treatment zone. Drill head 44 is placed at the end of turbine axis 43. Drill head 44 can be changed to perform different treatments apart from basic drilling. Preferably, a dense fluid is used to drive the turbine drill and allow heat generated by internal friction to dissipate. Sealed outer shaft 1 contains power fluid supply channel 2 and micro-turbine generator 3. Once power fluid supply channel 2 has passed through micro turbine generator 3, the fluid is delivered to the treatment zone. Functional device 4 is a laser in this embodiment. Device 4 assists drilling by pre-heating the dental material. This pre-heating reduces the amount of larger particles that break off while drilling and increases accuracy. Since fewer large particles break off while drilling, only the amount of dental material necessary to achieve the therapeutic effect is removed.

Optical fiber 10 and aspirating vacuum channel 6 are included in this hand-piece and fulfill the same purpose as those included in the description of FIG. 3. The distal end of power fluid supply channel 2 and the distal end of secondary supply channel 5 are designed to deliver fluids to the treatment areas. These channel systems can provide the treatment zone with disinfectant, anaesthetic, abrasive or PDT Substances. An unspecified number of additional fluid supply channels can be added to the hand-piece. The substances supplied by the fluid channels can be used at various stages of the drilling procedure to further enhance drilling accuracy and efficiency. For example, various abrasive particles can be used prior to drilling to simplify the drilling process. Particles in the fluid with radiation scattering properties may be used during drilling to enhance the laser treatment. Abrasive particles can also be used after drilling to improve adhesion of filling materials in the drilled holes. This improved adhesion reduces the incidence of cavities and micro-cracks.

EXAMPLE 3

Figure 5:
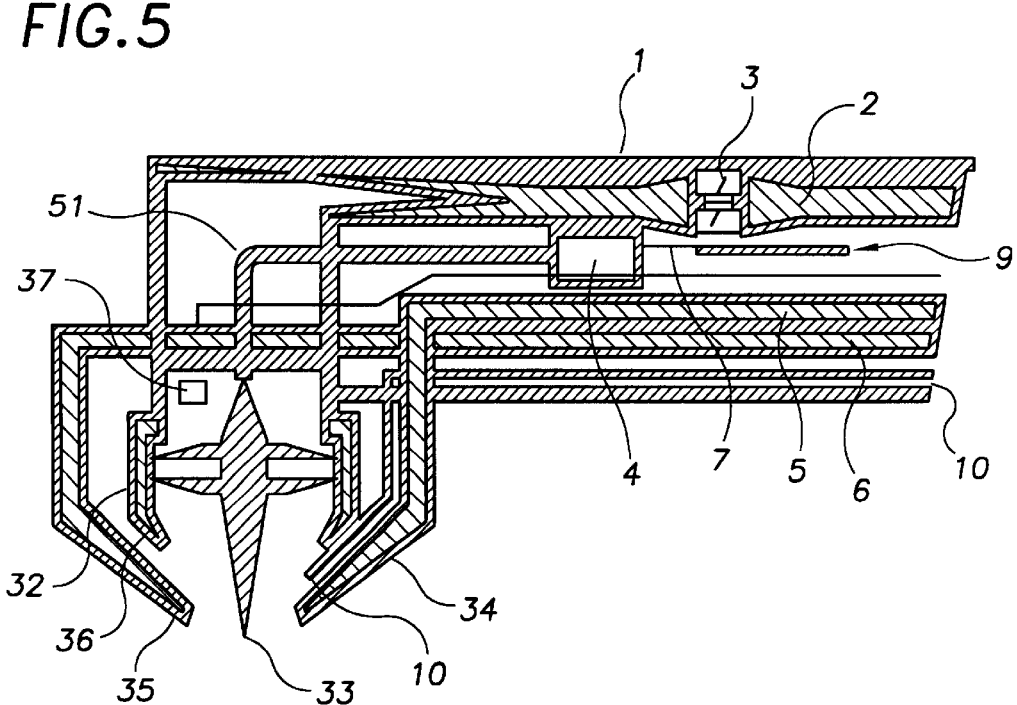
FIG. 5 shows an embodiment of a laser hand-piece cross section in which the radiation propagates via a light guide.

In the embodiment depicted in FIG. 5, the laser radiation does not directly propagate via optics to the treatment zone, but instead is coupled to a light guide. Light guide 51 may be a flexible optical fiber or a stiff wave-guide since the distance is small. Light guide 51 directs light to focusing optics 32. Focusing optics 32 project the radiation from light guide 51's distal end to treatment zone 33. Focusing optics 32 ensure adequate irradiation of the diseased areas. In the prior art a light guide must run all the way from an exterior control unit to the hand-piece. The present invention has several advantages over the prior art. Since the light source is contained within the hand-piece, the light guide does not need to be flexible. Furthermore, since the length is significantly shorter, there is a significant reduction in the risk of malfunction.

In another embodiment that is a variation of this example, it is possible to use multiple micro-turbine engines to drive multiple laser sources and combine the fibers of these laser sources to one fiber bundle. By combining these laser sources, the power provided to the treatment area can easily be increased. In order to keep the radiation at a high power density, it is important to choose a fiber with a minimal NA and a small core diameter. The embodiment also includes power-measuring device 37, which can be enclosed in several ways. In this hand-piece it is placed in such a way that it can detect the radiation that is back scattered from the surfaces of the optical system. Since the reflection from these surfaces relates linearly to the irradiated power, satisfactory control is possible. All other elements illustrated in FIG. 5 fulfill the same purposes as the corresponding elements in the previous example.

EXAMPLE 4

Figure 6:
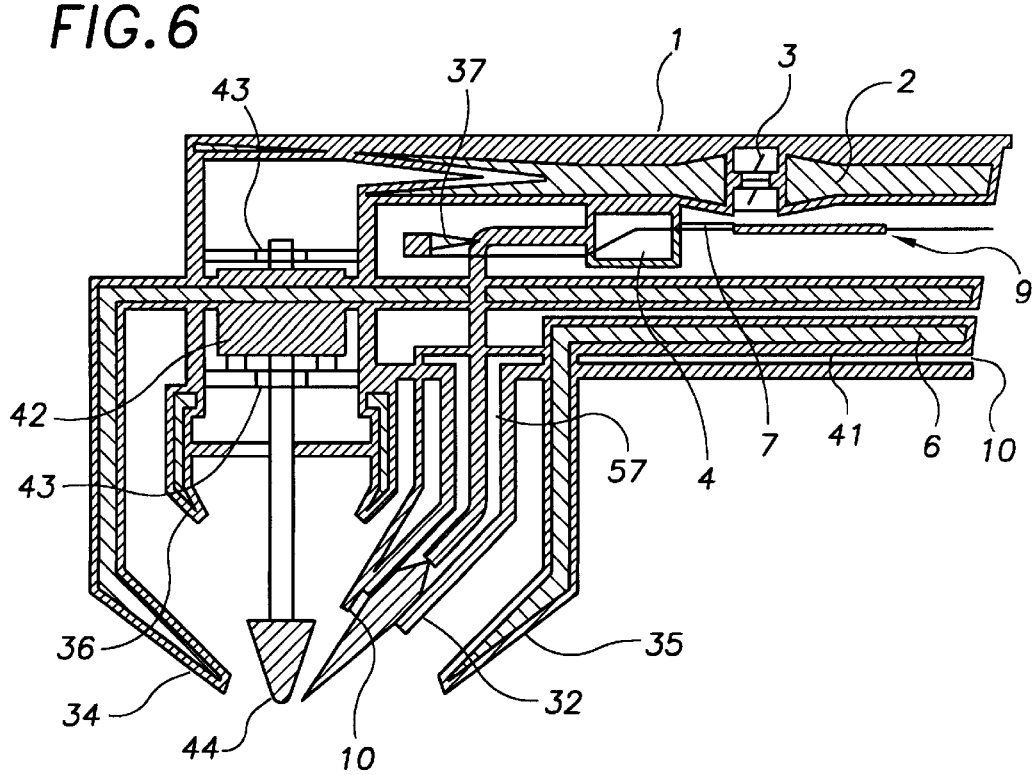
FIG. 6 illustrates a cross section of a hand-piece that combines a turbine driven laser coupled with an optical wave-guide and a conventional turbine drill.

Another embodiment of a laser and turbine drill handpiece is illustrated in FIG. 6. FIG. 6 depicts the principal changes that must be made to FIG. 4 if an optical waveguide is to be used. One or more light guides are coupled to a laser source. Since the distance between the laser and the treatment site is small, these light guides can be either flexible (i.e. fiber) or stiff. Light guide 51 directs the radiation to focusing optics 32. Optics 32 generate the correct irradiation for the particular treatment, such as laser radiation assisted drilling. In order to use a power detector with this embodiment, light guide 51 is prepared in a way to provide a small energy loss at its bend. Power measuring device 37 is placed behind this bend and the lost radiation measured gives a method of feedback and control.

EXAMPLE 5

FIG. 7 depicts a specialized hand-piece for the cauterization of a surgical treatment area. It is often necessary to cauterize the tissue to prevent blood loss after surgical procedures, such as vein or dental tissue treatments. The use of a light guide as introduced in FIGS. 5 and 6 is particularly useful for this application. The distal end of light guide 51 is directed toward the treatment area. Fiber tip 71, which is exchangeable, is placed on the distal end of light guide 51. Fiber tip 71 serves as the diffusing element. As described in previous embodiments, the hand-piece includes aspiration channel 6 and fluid channels 2,5, and 8, which are used to contribute to the treatment process. The system is monitored by power measuring device 37 that takes readings from a small energy loss area. Either direct bending of light guide 51 or removing the outer cladding from a small area creates the desired energy losses.

EXAMPLE 6

FIG. 8 depicts the preferred embodiment of a more sophisticated surgery tool that employs two lasers. Micro-turbine generator 3 drives two laser systems that are both coupled to light guides. The first laser is a tool for incisions. Light from this first laser travels along light guide 82 and is focused via focusing optics 32 onto the tissue. The second laser system follows the incision path of the first laser and disinfects/cauterizes the tissue to reduce any side effects or blood loss. In this second laser system, light guide 83 ends with diffusing fiber tip 81. Both light guides 82 and 83 are coupled to power detectors 37 at fiber bends. Optical fiber 10 is incorporated into the hand piece to allow imaging of the treatment area. Aspirating vacuum channel 6 is also included in the hand piece. Fluid supply channels 2 and 5 are also included and the fluid can be used on the treatment tissue as described in the prior embodiments. In an alternative embodiment, folding optics or direct radiation propagation can replace one or both of the light guides.

EXAMPLE 7

Figure 9:
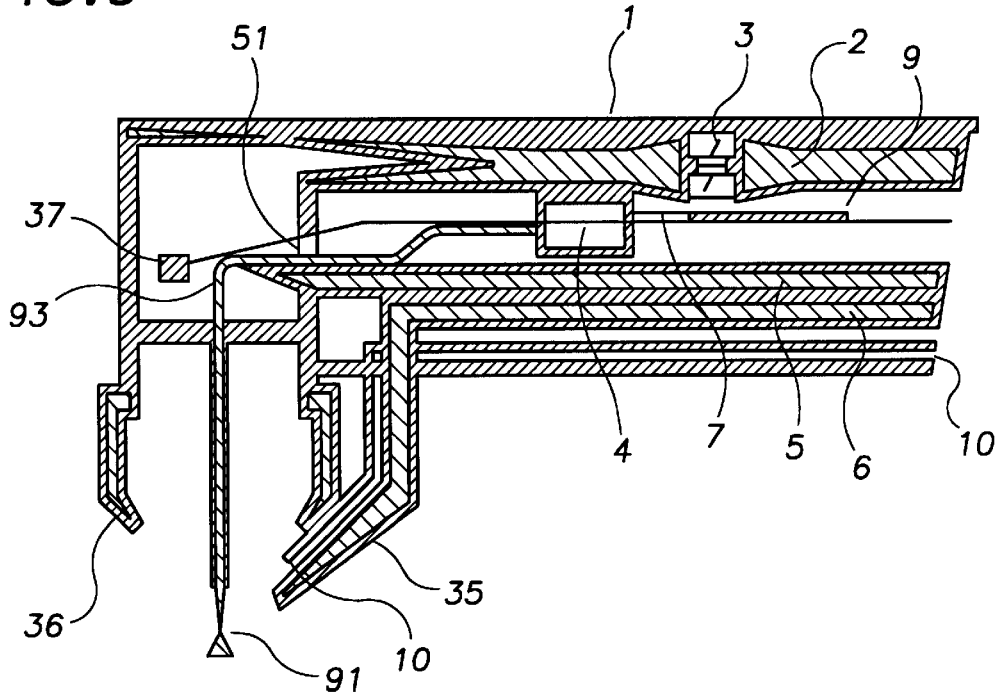
FIG. 9 shows an embodiment of a hand-piece cross section that generates a coupled laser and fluid beam.
Figure 9A:
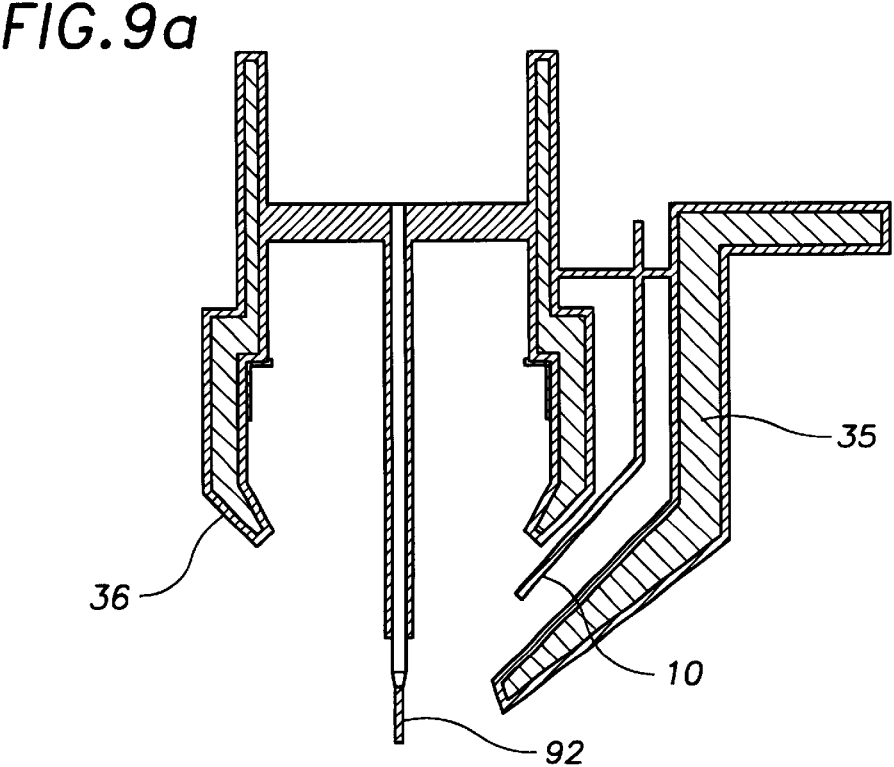
FIG. 9a shows an alternative tip for the coupled laser and fluid beam of FIG. 9 that will defocus the fluid and focus the light.

FIG. 9 shows a hand-piece that generates a coupled laser and fluid beam. As in the previous embodiments, the laser device is driven by energy from micro-turbine 3. Fluid from power fluid supply channel 2 is directed to the treatment site once it passes through turbine 3. This fluid can then be used either as a cooling medium or contain therapeutic compounds for the treatment site. Fluid light guide channel 93 leads through the hand piece head to the treatment zone. The fluid stream of either the micro-turbine engine driving fluid (channel 2) or independent fluid (channel 5) is coupled to fluid light guide channel 93. Fluid light guide channel 93 is designed to simultaneously be a fluid guide and a light guide. This can be achieved by choosing a channel material, whose refraction index is lower than the index of the fluid. Therefore, fluid light guide channel 93 also acts as an optical fiber. Both the fluid and the light beam are guided within fluid light guide channel 93. The distal end of fluid light guide channel 93 can be designed in at least four ways. It can be designed so that it will: focus the fluid and defocus the light, as in FIG. 9 with tip 91, defocus the fluid and focus the light, as in FIG. 9a with tip 92, or it will focus or defocus both elements respectively. The variation chosen is dependent on the specific treatment process. A focused laser beam or a focused water beam can be utilized for incision purposes. The defocused fluid beam can be used for disinfectant means, to assist the surgical process by cooling the environment, or in preparation for the surgical process. The defocused laser beam is an advantage if a larger region requires a lower dosage treatment. It is also possible to combine these variations with the previously mentioned abrasive procedures.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A dental hand-piece comprising;
   at least one micro-turbine generator driven by multipurpose fluids in gaseous or liquid form;
   at least one power fluid supply channel to deliver said multipurpose fluids to said micro-turbine generator;
   said micro-turbine generator generating electrical energy for powering at least one electricity consuming functional device;
   wherein said electricity consuming functional device is selected from the group; a compact laser, an electro-mechanical dental drill, an ultrasound generator, a microwave generator and, an activator for treatment chemicals; and
   each said hand-piece and said channels having a proximal and a distal end.

2. An apparatus according to claim 1 wherein said compact laser is selected from the group; a diode laser, a diode pumped solid state laser and a diode pumped frequency doubled laser.

3. An apparatus according claim 2 wherein radiation from said distal end at a treatment zone is imaged using an appropriate optics system at said distal end.

4. An apparatus according to claim 2 wherein radiation from said laser is coupled into an optical fiber.

5. An apparatus according to claim 2 wherein laser radiation is coupled into at least one optical fiber and guided therein to a treatment zone and said apparatus includes imaging optics for said at least one optical fiber at said distal end towards said treatment zone.

6. An apparatus according to claim 5 with at least one diffuser element at said distal end of said at least one optical fiber.

7. An apparatus according to claim 6 further comprising a second laser functional unit wherein the radiation from said second laser is transmitted to said treatment zone and focused through imaging optics.

8. An apparatus according to claim 2 further comprising a separate power fluid supply channel to drive a turbine drill at said separate supply channel's distal end and said apparatus includes means to transmit laser radiation to a treatment zone at said distal end.

9. An apparatus according to claim 8 wherein at least one additional supply channel to supply particles, either transparent or opaque, to enhance said laser's radiation effect is among a group of at least one supply fluid channels comprising said apparatus.

10. An apparatus according to claim 2 wherein radiation from said laser and said fluid of said at least one supply channel is coupled into a common fluid light guide with means for simultaneous delivery of fluid and light beams to said treatment area.

11. An apparatus according to claim 10 with a minimum of one extra fluid supply channel to supply further therapeutic substances.

12. An apparatus according to claim 1 further comprising at least one additional supply channel to deliver said multipurpose fluids to a treatment area.

13. An apparatus according to claim 1 wherein said at least one supply channel system comprises at least one channel to supply power fluid and at least one other channel to supply a fluid for photodynamic therapy purposes, and said apparatus includes means for directing said fluid for photodynamic therapy to a treatment zone.

14. An apparatus according to claim 1 further comprising at least one aspiration channel to remove excess fluid and particles from said treatment area.

15. An apparatus according to claim 1 further comprising at least one battery.

16. An apparatus according to claim 1 further comprising heat removal means using said multipurpose fluid.

17. An apparatus according to claim 1 wherein said at least one supply channel system supplies a fluid containing particles for abrasion and said apparatus includes suitable means at distal end of said channel for application of said fluid to said treatment zone.

18. An apparatus according to claim 17 wherein said abrasion particles are selected from group; a non transparent material, amorphous $SiO_2$, crystalline $SiO_2$, and ice.

19. An apparatus according to claim 1 with said at least one fluid supply channel having means to focus fluid at said distal end.

20. A dental clinical system incorporating a dental hand-piece as specified in claim 1, comprised of the following elements:
   a dental hand-piece as specified in claim 1,
   at least two fluid supply systems,
   at least one vacuum system for aspiration,
   at least one optical fiber port,
   a central control unit, and
   a foot piece to control treatment dependant parameters.

* * * * *